United States Patent [19]

Blake, II

[11] Patent Number: 4,604,356

[45] Date of Patent: Aug. 5, 1986

[54] PURIFICATION OF FLAVIN ADENINE DINUCLEOTIDE SYNTHETASE

[75] Inventor: Robert C. Blake, II, Elkhart, Ind.

[73] Assignee: Miles Laboratories, Inc., Elkhart, Ind.

[21] Appl. No.: 563,973

[22] Filed: Dec. 21, 1983

[51] Int. Cl.[4] ............................ C12N 9/12; C12Q 1/48
[52] U.S. Cl. ........................................ 435/194; 435/15
[58] Field of Search .......................................... 435/194

[56] References Cited

PUBLICATIONS

Biochemistry, vol. 15, No. 5, pp. 1043–1053 (1976).
Methods in Enzymology, vol. 18B, pp. 555–557 (1971).
Methods in Enzymology, vol. II, pp. 673–675 (1955).

*Primary Examiner*—Lionel M. Shapiro

*Attorney, Agent, or Firm*—Mary G. Boguslaski

[57] ABSTRACT

The invention provides a flavin adenine dinucleotide (FAD) synthetase preparation with a specific activity at 25° C. greater than at least 75 nanomoles per minute per milligram of protein in the preparation and usually greater than at least 150 nanomoles per minute per milligram of protein in the preparation as measured utilizing flavin mononucleotide (FMN) as the substrate. The purified preparation is obtained by disrupting a cellular source of FAD synthetase activity, precipitating the protein and separating an FAD synthetase active fraction by column chromatography. FAD synthetase catalyzes the reaction of adenosine triphosphate and flavin mononucleotide to flavin adenine dinucleotide and pyrophosphate, among others.

17 Claims, No Drawings

PURIFICATION OF FLAVIN ADENINE DINUCLEOTIDE SYNTHETASE

BACKGROUND OF THE INVENTION

I. Field of the Invention

The invention relates generally to protein purification; more specifically to enzyme purification. In particular, the invention provides a preparation and method for purification of the enzyme, flavin adenine dinucleotide (FAD) synthetase, preferably from microbial origin. FAD synthetase is formally designated ATP: FMN adenylyl transferase (EC 2.7.7.2) by the International Congress of Enzyme Nomenclature.

II. Description of the Prior Art

In general protein purification methods are applicable to enzyme purification. Such generally applicable methods are available in many literature references, see for example Biochemistry 2nd Ed., Lehninger, A., Worth Publishers, Inc. (1975). Affinity chromatography is one generally applicable method of protein purification. One variant of affinity chromatography is dye-ligand chromatography in which synthetic textile dyes are used as immobilized ligands. Use of these dyes in enzyme purification has gained wide acceptance since the late 60's. Many applications of dye-ligand chromatography have been made to the purification of adenosine triphosphate (ATP) binding enzymes. For example, Thompson et al, 72, Proc. Nat. Acad. Sci., USA, 669–672 (1975) described the purification of adenylate kinase, an ATP-binding enzyme, on Cibacron ®-Blue Sepharose with subsequent elution with ATP or adenosine diphosphate (ADP). However, few applications have been made to the purification of flavin-binding enzymes, such as FAD synthetase. In one case, Pompon et al., 110, Eur. J. Biochem., 565–570 (1980), purified the apoenzyme, apo(cytochrome b5 reductase) on immobilized Cibacron ®-Blue F3GA with subsequent elution with FAD or flavin mononucleotide (FMN). The apoenzyme is the active enzyme without its activating cofactor, FAD. Purification of the apoenzyme was used since most enzymes bind flavin too tightly to allow successful purification using dye-ligand chromatography with subsequent competitive elution. Moreover, the binding mechanism between the dyes and the enzymes is not fully understood and varies significantly from enzyme to enzyme and from dye to dye.

One measure of enzyme purity is its specific activity. As used herein the specific activity calculated for FAD synthetase is based on the ability of the enzyme to catalyze the reaction

$$\text{ATP} + \text{FMN} \xrightarrow[\text{metal cation}]{\text{FAD synthetase}} \text{FAD} + \text{pyrophosphate}$$

The units of specific activity used herein are nanomoles per minute per milligram, i.e., the enzyme preparation can produce the stated number of nanomoles of product, FAD, per minute per milligram of protein in the enzyme preparation used, at 25° C.

Since ATP and FMN are coenzymes in many biological reactions, their presence is an indication of the presence of biosystems in a sample. Further, the generation or consumption of these coenzymes in reactions can be used to diagnose particular clinical states. However, the concentration of ATP in biological fluids is often only $10^{-9}$ moles/liter (nanomolar) to $10^{-12}$ moles/liter (picomolar) so that highly sensitive assays are required. Enzymatic assays provide an advantage over stoichiometric assays since one molecule of enzyme can catalyze the formation of thousands of molecules of product. In order to take full advantage of this phenomenon, the enzyme preparation used should have as high a specific activity as possible.

Spencer, et al., Biochemistry, 15:5, 1043–1053 (1976) isolated FAD synthetase from a culture of Brevibacterium ammoniagenes (ATCC 6872). Their procedure involved (a) centrifuging broken bacterial cells; (b) separating the liquid fraction; (c) precipitating the protein in the liquid fraction with ammonium sulfate; (d) applying the precipitated protein in solution to a Sephadex ®-G-100 column and eluting. The FAD synthetase preparation obtained had a specific activity of 4.9 nanomoles per minute per milligram at 37° C. with radioactive flavin mononucleotide as the substrate.

SUMMARY OF THE INVENTION

A purification procedure has been devised which provides a FAD synthetase preparation which has at least about 15 times and usually about 30 times the specific activity of prior art preparations. The purified FAD synthetase preparation is prepared by a method which comprises the steps of (a) disrupting cells containing FAD synthetase activity; (b) separating the liquid fraction; (c) treating the separated liquid fraction with a protein precipitating agent; (d) separating the precipitated protein; (e) applying the precipitated protein in solution to a chromatography column containing a moiety selective for FAD synthetase; (f) eluting the column with a first eluting solution containing either (1) FMN or an analogue thereof, or (2) ATP or an analogue thereof and a divalent cation; and collecting a FAD synthetase active fraction; (g) applying the FAD synthetase active fraction to a chromatography column containing a molecular sieve capable of excluding molecules greater than at least about $10^5$ daltons, eluting and collecting a FAD synthetase active fraction; (h) applying the collected fraction to a second chromatography column containing a moiety selective for FAD synthetase; (i) eluting the second selective column with a second eluting solution containing the other of (1) FMN or an analogue thereof or (2) ATP or an analogue thereof and a divalent cation, not present in the first eluting solution as a second eluent, and collecting a FAD synthetase active fraction; and (j) removing the second eluent from the collected fraction. The procedure provides a FAD synthetase preparation with a specific activity greater than at least 75 nanomoles per minute per milligram, usually greater than at least 150 nanomoles per minute per milligram as measured at 25° C. with FMN as the substrate. FAD synthetase can be used in diagnostic procedures where ATP or FMN is the analyte or where a reaction with the analyte of interest consumes or generates ATP or FMN.

DESCRIPTION OF THE PREFERRED EMBODIMENTS

Protein purification generally depends on utilizing the physical and chemical properties of the desired protein to separate it from other proteins. Serial application to and elution from selective chromatography columns provides the basis of the purification method used herein. The focus of the invention is the choice of column materials and eluents.

Crude preparations having low FAD synthetase activity can be obtained from a variety of sources including mammalian tissue, such as rat or rabbit liver, fungi, and bacteria, such as Brevibacterium, Flavobacterium, Bacillus, and Psuedomonas. A convenient source is the bacteria, *Brevibacterium ammoniagenes* (ATCC 6872 in particular).

After a preparation having low FAD synthetase activity is obtained from mammalian sources or by growing and harvesting bacteria or fungi, the cell source is disrupted to release the enzyme. Disruption of the cells can be accomplished by a number of means, depending on the nature of the starting tissues or cells. Some common cell breakage methods include freeze-thaw, sonic oscillation, mechanical grinding (with or without an abrasive), ballistic homogenization, disruption in a pressure cell, or exposure to membrane-disrupting agents.

The liquid fraction of the resulting cell preparation is separated by methods such as centrifugation or filtration, and the separated liquid fraction is treated with a protein precipitating agent. Some common methods of protein precipitation include pH precipitation, organic solvent precipitation, and precipitation using inorganic salts; either divalent metal cations, such as zinc or magnanese, or antichaotropic anions, such as sulfate and fluoride. Ammonium sulfate, $(NH_4)_2SO_4$, is a preferred protein precipitating agent.

After the protein in the liquid fraction is precipitated, it can be separated by the methods discussed above. The separated protein is redissolved in buffer and residual protein precipitating agent is removed by dialysis. Any buffer with a buffering capacity around pH 6, such as sodium phosphate or 2-(N-morpholino)ethane sulfonic acid (MES) can be used. In a preferred embodiment sodium phosphate was used as the buffer.

The dialyzed protein solution is slowly applied to a chromatography column containing a moiety selective for FAD synthetase. At least three general types of moieties are selective for FAD synthetase: (1) natural substrates of FAD synthetase and their effective natural analogues; (2) synthetic analogues of the preceding; and (3) certain commercial textile dyes known as dye-ligands. The selective moiety chosen will often be an active-site directed ligand such as a natural substrate such as ATP, FMN, riboflavin or ADP, but their effective natural analogues such as adenosine monophosphate (AMP) and FAD can also be used. Synthetic analogues of these natural substrates or their effective natural analogues such as the deaza- or mercapto-substituted flavins, $\alpha,\beta$-methylene ADP, $\alpha,\beta$-methylene ATP, $\beta,\gamma$-methylene ATP or 5'-adenyl imidodiphosphate can also be used.

Dye-ligands generally are not as selective for FAD synthetase as the active-site directed ligands listed previously. However their low cost and commercial availability make them useful substitutes. Dye-ligands useful in the present purification scheme include Reactive Blue 2 (color index 61211), Reactive Green 12, Reactive Red 2 and Reactive Yellow 6. A particularly preferred dye-ligand, Reaction Blue 2, can be obtained from Ciba-Geigy, Ardsley, N.Y., under their trademark Cibacron ® Blue F36A.

The moiety selective for FAD synthetase, as chosen from any of the types listed above, is linked to an insoluble chromatographic support matrix by known chemical methods. Suitable chromatography support materials include cross-linked agarose, agarose, cellulose, cross-linked dextran and acrylamide agarose copolymer. A particularly preferred material is commercially available from Sigma Chemical Co., St. Louis, MO., as Rective Blue 2-Agarose. Other suitable materials are FMN-Agrose or ATP-agarose (both from Sigma Chemical Co., St. Louis, MO.).

One of FMN or ATP or analogues thereof, such as FAD, riboflavin or adenosine monophosphate is chosen as the principal component of the eluting solution for the first chromatography column selective for FAD synthetase. Preferably FMN is the principal eluent in the first eluting solution. The workable concentration range of FMN in the eluting solution is 1–7 mM. However, higher concentrations, 4 mM to saturation, are preferred; 6 mM is the concentration of choice.

After application to the first FAD synthetase selective column and elution, the FAD synthetase active fraction can be concentrated by methods including protein precipitation, ion exchange chromatography, and ultrafiltration. Ultrafiltration is a preferred method. Further separation is effected by applying the FAD synthetase active fraction to a chromatography column containing molecular sieve material capable of exluding molecules greater than at least about $10^5$ daltons and eluting. Suitable molecular sieve materials include Sephadex ®-G-100, Sephadex ®-G-200, Bio-Gel ® P-30, and Bio-Gel ® P-60; Sephadex ®-G-100 is a preferred material. A buffer solution as described previously is used as the eluting solution.

The FAD synthetase active fraction collected from the molecular sieve column is applied to a second chromatography column selective for FAD synthetase. The FAD synthetase-selective moiety in the second column can be the same or different from that in the first column selective for FAD synthetase and preferably is the same, i.e., Reactive Blue-2. If FMN or one of its analogues, such as FAD or riboflavin, is used as the principal element in the first eluting solution as preferred, then ATP or one of its analogues and a divalent cation are used as the principal eluent in the second eluting solution. Usually the divalent cation is chosen from the group zinc, manganese, magnesium, copper or cobalt.

ATP and magnesium cation are preferably included in the second eluting solution. The workable concentration range of ATP in the second eluting solution is 200 micromolar ($\mu M$) to 2 mM, with 400 $\mu M$ being the concentration of choice. The workable concentration range for magnesium cation in the second eluting solution is 1 mM to 100 mM, 10 mM being the concentration of choice.

After concentration as described previously, the second eluent can be removed from the collected fraction by several methods including ultrafiltration, protein precipitation, ion exchange chromatography, and chromatography on a molecular seive material capable of exluding molecules greater than at least about $10^5$ daltons. Chromatography on a molecular seive material such as Sephadex ®-G-100 purchased from Sigma Chemical Co., St. Louis, MO is a preferred method. The FAD synthetase active fraction obtained from the last purification step can be concentrated by methods described previously, resulting in the purified FAD synthetase active preparation.

Monitoring for the FAD synthetase active fractions during each chromatographic procedure is conducted by coupling the reaction of FMN and ATP catalyzed by FAD synthetase to FAD, to the reaction of FAD and an appropriate apoenzyme and following the production of the second enzyme with a reaction designed to produce a detectable response. Suitable apoenzymes and color indicator systems are described in the Italian Patent Application No. 4955A/83 filed on even date herewith, assigned to Miles Laboratories, Inc. and entitled; Enzymatic ATP and FMN Assay (Docket No. MS-1313).

The final FAD synthetase active preparation obtained has a specific activity at 25° C. greater than at least 75 nanomoles per minute per milligram of protein in the final preparation usually greater than at least 150 nanomoles per minute per milligram. (see Table I). The final preparation is commonly stored in a buffered solution at a lowered temperature with a preservative. Suitable preservatives include sodium azide, merthiolate and toluene.

The present invention will now be illustrated, but is not intended to be limited, by the following examples:

EXAMPLE

Purification of FAD synthetase active preparation

A. Materials

Protein precipitating agent:
Ammonium sulfate pellets.
FAD selective packing material:
Reactive Blue 2 covalently attached to cross-linked agarose (purchased as Reactive Blue 2—Agarose from Sigma Chemical Co., St. Louis, MO.)
Equilibration Buffer:
0.05M sodium phosphate, pH 7.0.
Molecular seive packing material:
Sephadex ®-G-100 purchased from Sigma Chemical Co., St. Louis, MO.
First Eluting Solution:
6 millimolar (mM) FMN in 0.5M sodium phosphate at pH 6.0.
Second Eluting Solution:
400 uM ATP and 10 mM $MgCl_2$ in 0.1M sodium phosphate buffer, pH 6.0.

B. Procedure

A culture of *Brevibacterium ammoniagenes* (ATCC 6872) was grown and harvested to provide a crude preparation containing FAD synthetase activity. The cells were then disrupted and the liquid fraction separated by centrifugation. The separated liquid fraction, dissolved in minimal 0.1 molar (M) sodium phosphate, was treated with a protein precipitating agent, ammonium sulfate, to reach 50% (w/v) saturation and the initial precipitate was discarded. The liquid fraction was again treated with ammonium sulfate to reach 80% (w/v) saturation. The precipitated protein was then dialyzed against 1 liter of 0.1M sodium phosphate at pH 7 over 2–3 days, changing the phosphate solution four times, to a total of 5 liters. All these operations were conducted at 4° C. However, subsequent operations up to storage were carried out at room temperature, 25° C.

A 9×5 centimeter chromatography column containing Reactive Blue-2 as the moiety selective for FAD synthetase (column material: Reactive Blue-2-Agarose, Sigma Chemical Co., St. Louis, MO.) was equilibrated with 0.05M sodium phosphate at pH 7 and then washed with 150 milliliters (ml) of the same solution at a flow rate of about 80 ml/hr. The solution of dialyzed precipitated protein was warmed to room temperature and applied slowly, over 2 hours.

The FAD synthetase active fraction was then eluted with the first eluting solution. The active fraction was obtained in the initial fractions containing FMN, and the majority of the activity was contained in a volume of 100–150 ml. The fractions containing enzymatic activity were subsequently pooled and concentrated to less than 10 ml using an Amicon Model 52 ultrafiltration device (Amicon Corporation, Lexington, MA) with a VM2 membrane.

The concentrated collected fraction was applied to a 60×2.5 cm column packed with Sephadex ®-G-100 as the molecular sieve and equilibrated with 0.05M sodium phosphate, pH 6.0. Elution was accomplished with the same equilibration buffer.

A 10×2.5 cm column containing the same FAD synthetase selective material (Reactive Blue-2-Agarose, Sigma Chemical Co., St. Louis, MO.) was equilibrated and washed as described previously. The fractions containing FAD synthetase activity were reapplied and the FAD synthetase active fraction was eluted with the second eluting solution. Again the FAD synthetase active fraction was collected.

After concentration to about 5 ml on the Amicon Model 52 ultrafiltration device, a final application to a Sephadex ®-G-100 column, as described previously, completed the purification procedure.

The active fraction from the final chromatography step was again concentrated using the Amicon device and was stored at 4° C. in 0.05M sodium phosphate, pH 6.0, containing 0.02% sodium azide as a preservative.

The Reactive Blue-2-Agarose columns were regenerated by washing with at least two column volumes of 8M urea, followed by washing with three column volumes of the equilibration buffer.

Protein Determination

Protein concentrations were determined by the Bradford assay, Bradford et al., *Anal. Biochem.* 72: 248–254 (1976) using bovine serum albumin as the standard protein. Bradford assays were performed on FAD-synthetase preparations at different stages in the purification. Results obtained after each chromatographic step are listed in Table I (column 1).

TABLE I

Purification Table for FAD-Synthetase

| After Treatment | Protein *mg | Activity nmoles FAD $min^{-1}$ | Specific Activity nmoles FAD $min^{-1} mg^{-1}$ |
|---|---|---|---|
| $(NH_4)_2SO_4$ precipitation (step d) | 2,600 | 1,040 | 0.49 |
| Reactive Blue 2-Agarose (FMN elution step f) | 77 | 770 | 10 |
| Sephadex ®-G-100, (step g) | 14 | 560 | 40 |
| Reactive Blue 2-Agarose (ATP-$MgCl_2$ elution step i) | 2.0 | 320 | 160 |
| Sephadex ®-G-100, (step j) | 1.2 | 210 | 180 |

Determination of Specific Activity of FAD Synthetase

FAD synthetase activity was measured by coupling the production of FAD through FMN and ATP to the reactivation of apo(glucose oxidase) to yield an active holoenzyme, glucose oxidase, whose activity could be monitored spectrophotometrically. The reaction scheme is as shown below:

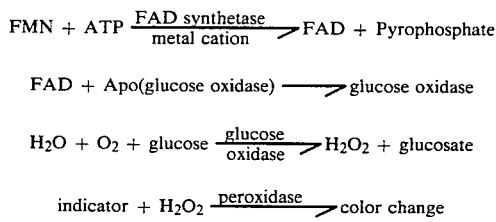

1. FMN + ATP $\xrightarrow[\text{metal cation}]{\text{FAD synthetase}}$ FAD + Pyrophosphate 2. FAD + Apo(glucose oxidase) $\longrightarrow$ glucose oxidase 3. $H_2O + O_2 + $ glucose $\xrightarrow[\text{oxidase}]{\text{glucose}}$ $H_2O_2$ + glucosate 4. indicator + $H_2O_2$ $\xrightarrow{\text{peroxidase}}$ color change

A. Materials

Apo(glucose oxidase) prepared according to the method described in U.S. Pat. No. 4,268,631, Ellis et al., horseradish peroxidase (Sigma Chemical Co., St. Louis, MO.). Other materials are commercially available.

B. Procedure 10 microliters ($\mu$l) of FAD synthetase was added to a 1-cm light path, disposable, polystyrene cuvette (Elkay Products, Inc., Worchester, MA) with a mixture containing 0.6 ml of a solution of 6.6 $\mu$M FMN, 0.1M sodium phosphate, 1.0 mM $MgCl_2$ and 50 $\mu$l of a solution of 8.0 mM 4-aminoantipyrine, 8.0 $\mu$M apo(glucose oxidase), and 50% (volume per volume, v/v) glycerol. A volume of 1.33 ml of a solution of 0.1M sodium phosphate, 300 $\mu$M ATP, 1.0 mM $MgCl_2$, 3.0 mM 2-hydroxy-3,5-dichlorobenzene sulfonate, 150 mM glucose, 1.5% (w/v) bovine serum albumin, 0.09 mg/ml peroxidase, and 0.01% (w/v) sodium azide was then added to the cuvette to initiate the reaction. The reaction mixture was incubated at 25° C., unless otherwise indicated. Absorbance measurements were performed at 520 nanometers (normally after ten minutes) on either a Beckman Model 3600 or a Bausch and Lomb Spectronic 200 double-beam spectrophotometer. Control assays containing no FAD-synthetase were always performed to assess the contribution to the observed absorbance change of residual glucose oxidase activity in the apoenzyme preparation.

Results are tabulated in Table I, column 2. The specific activities of the various products were calculated and are shown in Table I, column 3. The specific activity of the FAD synthetase preparation obtained by the purification procedure provided herein is reproducibly at least 15, and usually more than 30 times greater than that obtained by the Spencer procedure.

Obviously, many other modifications and variations of the invention as hereinbefore set forth may be made without departing from the spirit and scope thereof.

What is claimed is:

1. A method for purifying flavin adenine dinucleotide synthetase comprising the steps of:
    (a) disrupting cells containing flavin adenine dinucleotide synthetase activity,
    (b) separating a liquid fraction,
    (c) treating the separated liquid fraction with a protein precipitating agent,
    (d) separating the precipitated protein,
    (e) applying a solution of the precipitated protein to a chromatography column containing a moiety selective for flavin adenine dinucleotide synthetase,
    (f) eluting the chromatography column with a first eluting solution containing one of (1) flavin mononucleotide or an effective analogue thereof or (2) adenosine triphosphate or an effective analogue thereof and a divalent cation, as a first eluent, and collecting a fraction containing flavin adenine dinucleotide synthetase activity,
    (g) applying the collected fraction to a chromatography column containing a molecular sieve capable of excluding molecules greater than at least about $10^5$ daltons, eluting and collecting a fraction containing flavin adenine dinucleotide synthetase activity,
    (h) applying the collected fraction to a second chromatography column containing a moiety selective for flavin adenine dinucleotide synthetase,
    (i) eluting the second chromatography column with a second eluting solution containing the other of (1) flavin mononucleotide or an effective analogue thereof or (2) adenosine triphosphate or an effective analogue thereof and a divalent cation, not present in said first eluting solution, as a second eluent, and collecting a fraction containing flavin adenine dinucleotide cleotide synthetase activity, and
    (j) removing said second eluent from the collected fraction.

2. The method of claim 1 wherein the cells containing flavin adenine dinucleotide synthetase activity comprise a *Brevibacterium ammoniagenes* culture.

3. The method of claim 1 or 2 wherein the moiety selective for flavin adenine dinucleotide synthetase is a dye-ligand.

4. The method of claim 3 wherein the same dye-ligand is used in steps (e) and (h).

5. The method of claim 4 wherein the dye-ligand is Reactive Blue-2 (color index 61211).

6. The method of claim 1 wherein the first eluent is flavin mononucleotide.

7. The method of claim 6 wherein the concentration of flavin mononucleotide is from 4 millimolar to saturation.

8. The method of claim 7 wherein the second eluent is adenosine triphosphate and a divalent cation.

9. The method of claim 8 wherein the concentration of adenosine triphosphate is from 200 micromolar to 2 millimolar.

10. The method of claim 8 wherein divalent cation in the second eluting solution is magnesium cation.

11. The method of claim 1 wherein the removal of the second eluent is accomplished by use of a chromatography column containing a molecular seive capable of excluding molecules greater than at least about $10^5$ daltons.

12. A preparation of flavin adenine dinucleotide synthetase produced according to the method of claim 1 and having a specific activity of at least 75 nanomoles per minute per milligram of protein at 25° C. with flavin mononucleotide as the substrate.

13. A preparation of flavin adenine dinucleotide synthetase produced according to the method of claim 1 and having a specific activity of at least 150 nanomoles per minute per milligram of protein at 25° C. with flavin mononucleotide as the substrate.

14. A method for purifying flavin adenine dinucleotide synthetase comprising the steps of:
    (a) disrupting cells of a *Brevibacterium ammoniagenes* culture,
    (b) separating a liquid fraction,
    (c) treating the separated liquid fraction with a protein precipitating agent,
    (d) separating the precipitated protein, (e) applying a solution of the precipitated protein to a chromatography column containing Reactive Blue 2, (f) eluting the chromatography column with a first eluting solution containing flavin mononucleotide as a first eluent, and collecting a fraction containing flavin adenine dinucleotide synthetase activity, (g) applying the collected fraction to a chromatography column containing a molecular sieve capable of excluding molecules greater than at least about $10^5$ daltons, eluting and collecting a fraction containing flavin adenine dinucleotide synthetase activity, (h) applying said collected fraction to a second selective chromatography column containing Reactive Blue 2, (e) eluting the second chromatography column with a second eluting solution containing adenosine triphosphate and a divalent cation as the second eluent, and collecting a fraction containing flavin adenine dinucleotide synthetase activity, and (j) removing said second eluent from the collected fraction.

15. The method of claim 14 wherein the concentration of flavin mononucleotide in the first eluting solution is from 4 millimolar to saturation.

16. The method of claim 14 wherein the concentration of adenosine triphosphate is from 200 micromolar to 2 millimolar.

17. The method of claim 14 wherein the removal of the second eluent is accomplished by means of a chromatography column containing a molecular sieve capable of excluding molecules greater than at least about $10^5$ daltons.

* * * * *